United States Patent [19]

Söderberg

[11] 4,334,972
[45] Jun. 15, 1982

[54] AMPHOLYTE AND ITS USE IN SEPARATION PROCESSES

[75] Inventor: John L. Söderberg, Upsala, Sweden

[73] Assignee: Pharmacia Fine Chemicals AB, Upsala, Sweden

[21] Appl. No.: 199,232

[22] Filed: Oct. 21, 1980

Related U.S. Application Data

[63] Continuation of Ser. No. 64,359, Aug. 7, 1979, abandoned, which is a continuation of Ser. No. 891,105, Mar. 28, 1978, abandoned.

[30] Foreign Application Priority Data

Apr. 26, 1977 [SE] Sweden .................................. 7704783

[51] Int. Cl.³ ..................... B01D 57/02; C07C 101/00
[52] U.S. Cl. ................................. 204/180 R; 210/635; 210/656; 252/62.2
[58] Field of Search ............ 204/180 R, 180 G, 299 R, 204/180 S; 252/62.2; 560/205, 190, 171; 260/404, 404.5; 210/656, 659, 635

[56] References Cited

U.S. PATENT DOCUMENTS 3,692,654 9/1972 Svendsen ..................... 204/180 G X
4,131,534 12/1978 Just ............................. 204/180 R X Primary Examiner—Howard S. Williams
Attorney, Agent, or Firm—Fred Philpitt

[57] ABSTRACT

A water-soluble ampholyte which comprises the reaction product between
(a) one or more compounds selected from the group comprising certain amino-acids, hydroxylamine, an amine of the formula

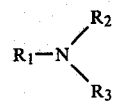

wherein $R_1$ is hydrogen, the group $H_2N-(CH_2)_n-$, wherein n is an integer 2-6, or the group $H_2N-(CH_2)_3-NH-(CH_2)_3-$, $R_2$ and $R_3$ are the same or different and each representing hydrogen, methyl, ethyl or hydroxyethyl or together with the intermediate nitrogen atom form certain heterocyclic groups, and certain di- and tripeptides, at least one of these compounds being one which contains at least one carboxyl group, or salts of the aforementioned compounds, and
(b) at least one bifunctional alkylating agent containing a straight or branched alkylene chain having 2-10 carbon atoms and which chain may be substituted with certain substituents and/or be broken by 1-3 oxygen atoms with certain conditions, in a molar relationship between (b) and (a) of 1:2-9:10.

8 Claims, No Drawings

AMPHOLYTE AND ITS USE IN SEPARATION PROCESSES

This is a continuation of application Ser. No. 64,359, filed Aug. 7, 1979 which in turn is a continuation of application Ser. No. 891,105 filed Mar. 28, 1978 both abandoned.

The present invention relates to a water-soluble ampholyte, for instance for separation purposes, as a buffer substance and/or a carrier electrolyte, and to a method for the manufacture of said ampholyte.

Ampholytes, i.e. mixtures of amphoteric substances, are being used more and more as so-called carrier ampholytes within the separation technique. Carrier ampholytes are particularly necessary for iso-electric focusing (an elctrophoretic technique). They are also valuable as buffer substances, for instance in chromatography processes, and as carrier electrolytes in, for instance, isotachophoresis. The first carrier ampholytes of greater interest comprised protein hydrolysates. H. Svensson (Acta Chem. Scand. 16 (1962) 456–466) has later suggested a synthetic mixture of 40 different amphoters. The first commercial product (Ampholine® from LKB-Produkter AB, Bromma, Sweden) comprises carboxyethylated oligomers of polyethyleneimine. A further commercial product (Servalyte® from Serva Feinbiochemica, Germany) comprises polyethyleneimineoligomers treated with propane sultone. All of these carrier ampholytes have the disadvantage that the conductivity and buffer capacity in the pH range 5–8 are very low with uneven focusing and local overheating as a consequence thereof.

The two aforementioned commercial products are synthesised from the extremely strong carcinogen ethyleneimine and the latter also from the strong carcinogen propane sultone. The manufacture of these ampholytes is therefore dangerous and expensive.

In electrophoresis the original ampholytes gave rise to pH-gradients between pH approximately 3 and pH approximately 10. Since narrower ranges are required, the pH 3–10-interval was fractionated to narrower part-intervals by preparative electrophoresis. The capacity of this method is low and the method is difficult and dangerous to carry out. It is possible to obtain straight pH-gradients by mixing such fractions of narrower intervals in certain proportions, although in this way larger quantities of superfluous ampholyte in uninteresting pH-intervals are obtained and must be discarded.

In accordance with the invention it has now surprisingly been found possible to manufacture in an inexpensive and simple manner carrier ampholytes which lack the disadvantages of the previously known ampholytes, and which are obtained directly in a product form and, upon electrophoresis, give rise to narrow pH-gradients, whereby the difficult and expensive preparative electrophoresis is eliminated. Products having wider pH-gradients can be obtained by mixing products according to the invention having different pH-gradients. The products according to the invention are also valuable as, on electrophoresis, they give a particularly uniform conductivity distribution over the pH-gradient of current interest.

In order for an ampholyte to function as a good carrier ampholyte, it is necessary that the buffer capacity at the isoelectric point (pI) is as high as possible. This can only be achieved when the pKa-values of the protolytic groups incorporated in the ampholytes are distributed in a narrow range around the isoelectric point. In carrier ampholytes known hitherto, the buffer capacity is spread over the whole of the pH-range 2–11, only a small part lying in the neighbourhood of the isoelectric point. (Further, the buffer capacities of known ampholytes are often unevenly distributed in a manner such that they are maximal in the range 3–4 and 8.5–9.5).

The isoelectric point of an amphoter normally lies centrally between or approximately centrally between two sequential pKa-values. Thus, the isoelectric point always lies at a local minimum in the buffer capacity, which further emphasises the necessity of having the pKa-values lying narrowly collected around pI.

Earlier processes have been based on the concept that the introduction of many protolytic groups in a molecule cause wide spreading of the pKa-values and that it is impossible to concentrate the pKa-values around a specific point (see for example, Swedish Patent No. 314,227 or the corresponding U.S. Patent No. 3,485,736).

By means of the present invention it has been found possible to synthesise directly ampholyte mixtures having isoelectric points within narrow ranges and, at the same time, have narrowly lying pKa-values and therewith also a high buffer capacity at pI.

When, for example, glutamic acid and aspartic acid are copolymerised with epichlorohydrin it is found that the pKa-values of the carboxyl groups only change some tenths of a pH-unit. Both aspartic acid and glutamic acid have two carboxyl groups and one amino group, the pI lying centrally between the pKa-values of the carboxyl groups.

| Amino acid | $pKa_1$ | $pKa_2$ | $pKa_3$ | pI |
|---|---|---|---|---|
| aspartic acid | 2.1 | 3.9 | 9.8 | 3.0 |
| glutamic acid | 2.2 | 4.3 | 9.7 | 3.3 |

In the copolymerisation, oligomers having isoelectric points substantially between pH 3.0 and 3.3 occur, i.e. the range is limited by the pI of the monomeric amino acids present. With each pI obtained the "distance" to the nearest pKa-value is less than one pH-unit. Furthermore two thirds of all protolytic groups buffer at pI. The number of different amphoters becomes very high. If there is used d,l-aspartic acid and d,l-glutamic acid, which are copolymerised with d- or l-epichlorohydrin to solely hexamers, 1680 different amphoters are generated within a pH-range of 0.3 pH-units. This exceeds by a very wide margin what has previously been achieved. The number of "good" amphoters (i.e. amphoters, wherein the distance between pI and the pKa-value closest thereto is $\leq 1$ pH-unit) is approximately 10 times larger than what was previously obtained for the whole of the pH-range 3–10 for commercially available products. If d,l-epichlorohydrin is used, more than 50,000 different amphoters are obtained, that is more than 300 times more amphoters than in carrier ampholytes previously known. An enormous great number of amphoters can be obtained in the mixture by polymerising more than two components.

By mixing in in the polymerisation process more or other amino dicarboxylic acids it is possible to obtain other pH-ranges of different lengths within the range 2–4. The pH-range 4–5 is covered by mixing amino carboxylic acids with amino dicarboxylic acids. The extent of the pH-range can also be adjusted somewhat by changing the degree of polymerisation. A higher degree of polymerisation results in a more narrow range.

In an analogous manner as that applied with amino dicarboxylic acids, diamino carboxylic acids can be polymerised to ampholytes which cover narrow pH-ranges, but then on the alkaline side. For example, it is possible to obtain ampholytes which cover the pH-range 9.5–10.5, by copolymerising d,l-arginine and d,l-lysine with epichlorohydrin. The situation on the alkaline side is more complicated, since the pKa-values are changed for those amino groups which are alkylated by the polymerisation reactant (e.g. epichlorohydrin or 1,3-dibromopropane). Certain amino groups can be protected by polymerising at a suitable pH, the pKa-values of these amino groups remaining substantially unchanged.

An important factor is that the pKa-value can be predicted when alkylating under polymerisation. In this way it is possible to design a synthesis in a manner such that pKa-values are generated in an interesting pH-range where the starting substances lack buffer capacity. The following table is used as a starting point for the discussion:

|  | $pKa_1$ | $pKa_2$ | $pKa_3$ | $pKa_4$ |
|---|---|---|---|---|
| $\begin{array}{c}\text{CH}_2\text{—CH}_2\text{—CH}_2 \\ \mid \qquad\qquad\qquad \mid \\ \text{H}_2\text{C—NH} \qquad \text{NH}_2 \\ \mid \\ \text{H}_2\text{C} \\ \mid \\ \text{H}_2\text{C—NH} \qquad \text{NH}_2 \\ \mid \qquad\qquad\qquad \mid \\ \text{CH}_2\text{—CH}_2\text{—CH}_2\end{array}$ | 10.6 | 10.0 | 8.7 | 7.4 |
| $\begin{array}{c}\text{CH}_2\text{—CH}_2 \\ \mid \qquad\qquad \mid \\ \text{H}_2\text{C—NH} \quad \text{NH}_2 \\ \mid \\ \text{H}_2\text{C—NH} \quad \text{NH}_2 \\ \mid \qquad\qquad \mid \\ \text{CH}_2\text{—CH}_2\end{array}$ | 9.8 | 9.3 | 6.7 | 3.6 |

It will be seen from the table that when the nitrogen atoms are separated by two (2) carbon atoms, the distance between the lowest and the highest pKa-value is about six (6) pH-units. When the number of nitrogen atoms increases, the width of the range also increases, whilst at the same time there is obtained a depletion in the pH-range 5–8.

It will also be seen from the table that when the nitrogen atoms are separated by three (3) carbon atoms, the distance between the lowest and highest pKa-values is only approximately three (3) pH-units. When the number of nitrogen atoms increases in homologous series the width of the range, surprisingly enough, is not changed to any appreciable extent.

Sequences of this latter type (i.e. having three carbon atoms between the nitrogen atoms) occur when ammonia or amines are polymerised with, e.g., 1,3-dibromopropane. If the polymerisation is carried out with, e.g., epichlorohydrin, a hydroxyl group is introduced on the centre carbon atom of each link. These β-hydroxyl groups cause a systematic shifting of the whole of the pKa-range without increasing the width. Instead of landing between approximately 7.5 and 10, as in the Example, the range becomes approximately 6–9. If the amino groups in the polymer are substituted, further systematic shifting of the pKa-values is obtained. For example, N(6-carboxyhexyl)- results in no appreciable change in the pKa-value, N(2-carboxyethyl)- results in a lowering of <0.5 pH-units, N-carboxymethyl- results in a lowering of ~0.5 pH-units, and N(N'-carboxymethylamidomethyl)- (i.e. HOOC—CH$_2$—CO—CH$_2$—) results in a lowering of ~1 pH-unit. A lowering greater than roughly 1.5 pH-units is obtained by substitution with, e.g., N-hydroxy groups or N-nitrilomethyl groups. The polymers shown in the example above are most simply obtained by polymerising the following amino acids with an epihalohydrin: 6-aminohexanoic acid, β-alanine, glycine, glycylglycine, hydroxylamine and aminoacetonitrile. In order for pI for the polymers to be located in the ranges of interest (the ranges having a high buffer capacity) the proportions between amino groups and carboxyl groups must be adjusted, in this case with a surplus of amino groups. This is done in a manner such that the amino acid or amino acids is or are copolymerised with amines. Ammonia is used in the simplest case. If it is desired to lower pKa, e.g. 0.5 pH-units, 2-aminoethanol can be used for example, while if it is desired to increase pKa a corresponding amount, ethylamine can be used for example. As alternative to amines, diaminomonocarboxylic acids can be used, e.g. histidine and lysine. At a high reaction-pH (10) both amino groups are polymerised in lysine, while with a lower pH (8.5) only the α-amino group is alkylated in the polymerisation, whilst the pKa-value of the other amino group is marginally affected. A similar result is obtained if ethylenediamine is polymerised at different pH values. An alternative method of protecting the pKa-value of an amino group in a diamino compound is to ethylate the compound prior to polymerisation. For example copolymerisation of amino acids with N,N-diethylaminoethylamine.

Thus, ampholytes having pI-values within the range of 0.5–3 pH-units can be prepared by direct synthesis using the aforedescribed method. If it is desired to obtain a pI-range between, e.g., pH 2.5 and 10.5, a plurality of narrow ranges can be mixed. Such a mixture may then contain thousands to tens of thousands of different amphoters, for instance, more than about one thousand to, for instance, about 100,000 or more, for instance about 10,000 different amphoters.

The ampholyte according to the invention is characterised in accordance with the above by the fact that it comprises the reaction product between (a) one or more compounds selected from a group containing amino-acids, hydroxylamine, an amine of the formula

in which R$_1$ is hydrogen, the group H$_2$N—(CH$_2$)$_n$—, wherein n is an integer 2–6, or the group H$_2$N—(CH$_2$)$_3$—NH—(CH$_2$)$_3$—, R$_2$ and R$_3$ are the same or different and each representing hydrogen, methyl, ethyl or hydroxyethyl or together with the intermediate nitrogen atom form an imidazolyl, morpholinyl or piperazinyl group, and di- and tripeptides, said amino acids and di- and tripeptides containing at least one nitrogen atom having one or two hydrogen atoms bound thereto and not containing other aromatic groups than imidazolyl and having a molecular weight of at most 200, at least one of these compounds being one which contains at least one carboxyl group or salts of the aforementioned compounds, and (b) at least one bifunctional alkylating agent containing a straight or branched alkylene chain having 2-10 carbon atoms, preferably 3 or 6-10 carbon atoms, which chain is optionally substituted with 1-3 hydroxyl groups and/or 1-3 carboxyl groups and/or is broken by 1-3 oxygen atoms, at most one other atom than carbon and hydrogen being bound to one and the same carbon atom in the alkylene chain, in a molar relationship between (b) and (a) of 1:2-9:10, preferably 2:3-7:8.

The invention also relates to a method for preparing the aforementioned ampholyte.

The method according to the invention is characterised by reacting (a) one or more compounds from a group including amino acids, hydroxyl amine, an amine of the formula

in which $R_1$ is hydrogen, the group $H_2N-(CH_2)_n-$, where n is an integer 2-6, or the group $H_2N-(CH_2)_3-NH-(CH_2)_3-$, $R_2$ and $R_3$ are the same or different and each representing hydrogen, methyl, ethyl or hydroxyethyl or together with the intermediate nitrogen atom form an imidazolyl group, a morpholinyl group or a piperazinyl group, and di- and tripeptides, said amino acids and di- and tripeptides containing at least one nitrogen atom having one or two hydrogen atoms bound thereto and not containing other aromatic groups than imidazolyl and having a molecular weight of at most 200, at least one of these compounds being one which contains at least one carboxyl group, or salts of the aforementioned compounds and (b) at least one bifunctional alkylating agent containing a straight or branched alkylene chain having 2-10 carbon atoms, preferably 3 or 6-10 carbon atoms, which chain is optionally substituted with 1-3 hydroxyl groups and/or 1-3 carboxyl groups and/or broken by 1-3 oxygen atoms, at most one other atom than carbon and hydrogen being bound to one and the same carbon atom in the alkylene chain, in a molar ratio between (b) and (a) of 1:2-9:10, preferably 2:3-7:8.

The amino acids used as the starting material for the carrier ampholyte according to the invention can, in principle, by any naturally occurring amino-acid or any synthetic amino-acid containing one, or preferably two, hydrogen atoms bounds to a nitrogen atom and not containing other aromatic groups than imidazolyl and having a molecular weight of at most 200. Examples of such amino acids are glycine, alanine, β-alanine, sarcosine, serine, cysteine, cysteic acid, α-aminobutyric acid, β-aminobutyric acid, γ-aminobutyric acid, α-aminoisobutyric acid, glycyl-glycine, asparagine, aspartic acid, homocysteine, threonine, homoserine, glutamine, glutamic acid, hydroxyglutamic acid, valine, isovaline, norvaline, methionine, pentahomoserine, ε-aminocaproic acid, leucine, isoleucine, norleucine, cystine, lysine, histidine, hexahomoserine, diaminosuccinic acid, and arginine. Preferred amino-acids from this list are glycine, β-alanine, glycyl-glycine, aspartic acid, glutamic acid, lysine, serine, ε-aminocaproic acid, histidine, diaminosuccinic acid and arginine.

As an example of salts of the compounds listed under (a) above can be mentioned acid addition salts with mineral acids, e.g. HCl and $H_2SO_4$ and alkali metal salts (e.g. sodium and potassium salts). Preferably the d,l-form of the amino acids and of the other reactants according to (a) and (b) above is selected to avoid optical activity of the reaction product and to increase the number of amphoters in the obtained mixture of amphoters. Although when the product is not required to be optically inactive, reactants of d-form or l-form may be used.

Examples of amines of the formula

for use as the starting material for carrier ampholytes in accordance with the invention are ammonia, methylamine, dimethylamine, ethylamine, diethylamine, methylethylamine, hydroxyethylamine, methylhydroxyethylamine, N,N-diethylenediamine, N-ethylethylenediamine, imidazole, morpholine, N-aminoethylmorpholine, piperazine and aminoethylpiperazine.

Examples of dipeptides and tri-peptides for use as starting material for the carrier ampholytes according to the invention include glycylglycine, glycylglycylglycine, and the dipeptides and tripeptides which can be formed by the aforementioned preferred amino acids whilst limiting the molecular weight to at most 200.

Preferably at least two (for instance at least three) of the compounds containing amino groups mentioned under (a) above are used in the synthesis of ampholytes according to the invention in order to obtain a great number of amphoters in the ampholytes. In this connection a great number of such amino compounds may be contemporaneously used in the synthesis although, for practical reasons, for instance a number less than 20 is generally chosen.

Examples of bifunctional alkylating agents for use in accordance with the invention include compounds of the type X—A—Y, where X and Y are the same or different and each designates a halogen atom, preferably chlorine or bromine, and A represents a straight or branched alkylene chain having 3-10 carbon atoms and being optionally substituted with 1-3 hydroxyl groups and/or 1-3 carboxyl groups and/or broken by 1-3 oxygen atoms, or a corresponding epoxide compound which can be obtained from the compound of the aforementioned formula by splitting-off hydrogen halide. Of these compounds, those containing 3 or 6-10 carbon atoms are preferred. Particularly preferred compounds are those containing 3 or 6 carbon atoms, particularly epihalohydrins, 1,3-dihalo-2-propanols and 2,3-dihalo-1-propanols, i.e. compounds of the formulae

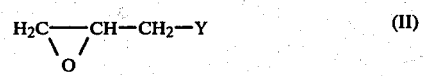

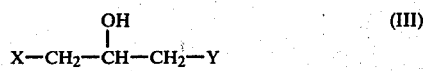

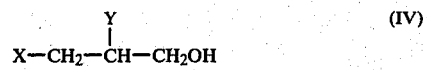

in which X and Y have the aforestated significance. Examples of bifunctional alkylating agents of the type X—A—Y according to the above include epichlorohydrin, epibromohydrin, 1,3-dichloro-2-propanol, 1,3-dichloropropane, 1,2-3,4-diepoxybutane, diglycidyl ether, 1,2-ethanedioldiglycidyl ether, 1,4-butanedioldiglycidyl ether, glycerol-1,3-diglycidyl ether, and 1,3-dibromo-2-carboxypropane.

For practical reasons only one or two such bifunctional alkylating agents (i.e. bridge-forming agents) according to (b) above is or are often used in the synthesis but a greater number of different such bridge-forming agents may, of course, be used in one and the same synthesis.

Ampholytes according to the invention are prepared in accordance with the method according to the invention by reacting one or more compounds of the group listed under (a) above with at least one bifunctional alkylating agent listed under (b) above in a molar relationship between (b) and (a) of 1:2–9:10, preferably 2:3–7:8, at least one of the compounds under (a) being one which contains at least one carboxyl group. Suitably of the different compound groups under (a) above are combined two amino-acids, one amine, and one dipeptide or tripeptide, or two amines, one amino-acid and one dipeptide or tripeptide, although fewer or more components can be chosen in combination. Examples of combinations of compounds from the group (a) are:

Glycine, $\beta$-alanine, ammonia and glycylglycine;
glycine, $\beta$-alanine, ethylenediamine and glycylglycine;
glycine, $\beta$-alanine, ethylenediamine, N,N-diethylethylenediamine and glycylglycine;
arginine, glycine, $\beta$-alanine, ammonia, N,N-diethylethylenediamine and glycylglycine;
aspartic acid, $\beta$-alanine and glycylglycine;
glutamic acid, $\beta$-alanine and glycylglycine;
mesodiaminosuccinic acid, aspartic acid and glycylglycine;
aspartic acid, 6-aminohexanoic acid and glycylglycine;
glycine, $\beta$-alanine, imidazole and glycylglycine;
ammonia, hydroxylamine, glycylglycine, and subsequent treatment with Na-chloroacetate;
valine, glutamic acid and serine;
hexamethylenediamine, 1,4-diaminobutane, 1,3-diaminopropane and
glycylglycine, and subsequent treatment with sodium chloroacetate;
piperazine, bis-(3-aminopropyl)-amine and glycylglycine, and
subsequent treatment with sodium chloroacetate;
aminoethylmorpholine, aminoethylpiperazine, piperazine and
glycylglycine and subsequent treatment with sodium chloroacetate;
dl-aspartic acid and dl-glutamic acid;
histidine, $\alpha$-aminobutyric acid and ammonia;
asparagine, $\beta$-alanine, methylamine and alanylglycine;
glutamine, $\beta$-aminobutyric acid, ammonia and alanylalanine;
threonine, $\beta$-alanine, ethylamine and glycylalanine;
methionine, $\beta$-alanine, ammonia and glycylglycylglycine;
cysteic acid, $\beta$-alanine and glycylglycine;
glycine, $\beta$-alanine, ammonia and alanylalanylglycine;
glycine; $\beta$-alanine, ammonia and glycylalanylalanine;
glycine, $\beta$-alanine, ammonia and alanylalanylalanine.

The reaction between the components (a) and (b) is carried out in water, dimethylsulphoxide, dimethylformamide, methanol, ethanol and similar solvents or mixtures thereof. The reaction is suitably carried out in an alkaline medium, for instance, at a pH of from 9 to 11, and at a reaction temperature of, for instance, 20° to 50° C., preferably 30° to 50° C. Generally, the reaction time is from 3 to 20 hours depending upon the choice of starting material and reaction temperature; as is well known, a higher reaction temperature enables the reaction time to be shorter. The reaction is terminated by neutralising with a strong acid, e.g. HCl. The reaction solution obtained is de-salted, e.g. by gel-filtration.

In accordance with one embodiment of the invention, the reaction product between the components (a) and (b) can be subsequently treated with a halogenated (preferably in $\alpha$-position) lower aliphatic mono-, di-, or tri-carboxylic acid with 2 to 6 carbon atoms, preferably a haloacetic acid, for instance chloroacetic acid, bromoacetic acid or iodoacetic acid, preferably in the form of a salt with an alkali metal (e.g. sodium or potassium). This subsequent treatment is carried out directly on the reaction mixture obtained from the above reaction prior to neutralisation and without intermediate isolation of the reaction product. Said subsequent treatment is carried out at a temperature of 10° to 80° C., preferably at room temperature and over a period of time which may vary from approx. 24 hours in the lower part of the temperature range to approx. 4 hours in the upper part of said range. Neutralisation and de-salting as above are carried out subsequent to said treatment.

If desired, the obtained mixture of amphoters may be fractionated. Fractionation may, for instance, be carried out by means of ultrafiltration, gel filtration, ion exchange chromatography, adsorption processes, electrophoresis or fractionated precipitation.

In this connection there may, for instance, be obtained a mixture having a narrower molecular weight distribution and/or adjusted range width of pI-values and/or having a more uniform conductivity distribution.

Small amounts of unreacted starting substances possibly occurring may also be removed by the fractionation.

The mixture of amphoteric substances according to the invention contains preferably no or only to a smaller part (for instance less than 10% by weight) molecules having a molecular weight above 1500, preferably 1000, for instance 800 or 700.

The molecular weight distribution is preferably chosen such that more than 90% by weight of the mixture falls within the molecular weight range of 100 to 1500, preferably within the range 150 to 1000 such as 200 to 800.

The weight average molecular weight ($M_w$) generally lies within the range 300 to 800, for instance within the range 350 to 700, e.g. 400 to 600, 1 such as 400 to 500, and the number average molecular weight ($M_n$) generally lies within the range 200 to 500, for instance within the range 300 to 400.

The above mentioned molecular weight data are based on analytical gel filtration with polyethyleneglycols as standards.

According to the invention products having a low (and also even) light absorption in the visible range as well as in the UV-range (for instance at 280 nm) over a wide pH-range can be obtained.

The products according to the invention have been found to possess very favourable properties in, for instance, isoelectric focusing and isotachophoresis and as carrier electrolytes and/or buffers, for instance in various biochemical investigations.

The invention will now be further illustrated with reference to a number of Examples, although it will be understood that these Examples are not limitative of the scope of the invention, as it is defined in the accompanying claims.

EXAMPLE 1

0.23 mole of ammonium chloride, 0.185 mole of β-alanine and 0.184 mole of glycine and 150 ml of distilled water were charged to a 3-necked round flask provided with an agitator, thermometer, two drip funnels and a pH-electrode. When all the solid substances had dissolved, 0.23 mole of sodium hydroxide was added. One of the drip funnels contained a specific quantity of 10% sodium hydroxide solution. and this solution was charged dropwise to the flask until the pH of the reaction mixture was 10.0. 0.50 mole of epichlorohydrin was slowly added dropwise from the other drip funnel. At the same time sodium hydroxide solution from the first drip funnel was added in order to ensure that the pH did not fall beneath 10.0. The drip speed was controlled in a manner to ensure that the temperature did not exceed 50° C.

Subsequent to completing the charge of epichlorohydrin, the reaction was permitted to continue overnight at room temperature. The quantity of sodium hydroxide charged to the flask was carefully determined by measuring the amount remaining in the drip funnel, whereafter a corresponding quantity (in mole) of hydrochloric acid was added to the synthesis. Subsequent to the neutralisation, the whole synthesis was de-salted by chromatography on a column containing 7.5 l of Sephadex ® G-15 (beads of dextran cross-linked with epichlorohydrin; from Pharmacia Fine Chemicals AB, Uppsala, Sweden). The eluent used was distilled water. Fractions of 250 ml were taken and the amount of ampholyte in these fractions was determined by titration on 1 ml samples between pH 4 and 7. The salt content of the fractions was determined by conductivity measurement. Those fractions which contained ampholyte but which did not contain salt were vaporised under vacuum until 1 ml of the solution consumed 1.0 mmole of sodium hydroxide when titrating between pH 4 and 7.

The product was tested as a carrier amopholyte in isoelectric focusing. To this end there was prepared a thick suspension by mixing 6.25 ml of ampholyte solution having a sodium hydroxide buffering capacity of 1.0 mmole per ml of solution between the aforementioned pH limits with 7.50 g of Sephadex ® G-75 Superfine (beads of dextran cross-linked with epichlorohydrin; from Pharmacia Fine Chemicals AB, Uppsala, Sweden) and with 86.25 ml of distilled water. (Alternatively, a 12.5% solution of sucrose in distilled water can be used instead of water.) Air was then vented from the suspension under vacuum for approx. 5 minutes, whereafter a layer of the suspension 1 mm thick was spread onto a thin glass plate 12.5×25 cm in dimension. At a distance of 23 cm from each other on the plate, there were placed two strips of filter paper (12.5×0.5×0.3 cm in dimensions) of which one contained 1-M sodium hydroxide solution and the other 1-M sulphuric acid. The glass plate was then placed on the cooling plate of a flat-bed electrophoresis apparatus. Platinum metal electrodes were placed on the filter paper strips. The electrode in contact with the sulphuric acid was connected to the positive terminal of a so-called constant-effect power supply. The other electrode was connected to the negative pole. The power unit was set to 15 watts and the terminal voltage at 2000 Volts. The electrophoresis was continued for 6 hours.

Upon completion of the electrophoresis, the pH was measured at each centimeter between the electrode strips with the aid of an Ingold surface electrode. A diagram of pH as a function of the distance from the cathode was drawn, whereafter the interval lengths were measured thereon. As a result there was obtained a straight pH-gradient between pH 4 and 7 which encompassed 85% of the distance between the electrode solutions.

The ampholyte was also tested as a one percent solution in the column technique described by H. Svensson (Archives of Biochemistry and Biophysics, Supplement 1, pages 132–138, 1962). The column was eluated through a UV-monitor (LKB-Uvicord III) and through a conductivity-monitor (Chromatronix) and so curves of ultraviolet absorption and conductivity were obtained as function of pH. The conductivity was found to be low and extremely uniform over the pH-range from 4 to 7. Also the ultraviolet absorption was low and extremely even.

EXAMPLE 2

This experiment was carried out in the same manner as that described in Example 1, but with the following charge of chemicals:
0.100 mole of ammonium chloride
0.250 mole of glycine
0.250 mole of β-alanine
0.100 mole of NaOH.

When isoelectric focusing in the manner described in Example 1, there was obtained a pH gradient between pH 4 and 6 which covered 75% of the distance between the electrode solutions.

In column technique as described in Example 1 uniform and low conductivity and UV-absorption curves were obtained over the pH-range 4 to 6.

EXAMPLE 3

This experiment was carried out in the same manner as that described in Example 1, but with the following amines and amino acids:
0.110 mole of ethylenediamine
0.245 mole of β-alanine
0.184 mole of glycine
0.0613 mole of glycylglycine.

When isoelectric focusing there was obtained a pH-gradient between pH 4 and 8, which covered 87% of the distance between the electrode solutions.

In column technique as described in Example 1 uniform and low conductivity and UV-absorption curves were obtained over the pH-range 4 to 8.

EXAMPLE 4

This experiment was carried out in the same manner as that described in Example 1, but with the following amino acids;
0.2 mole of glycine
0.2 mole of glycylglycine
0.30 mole of β-alanine.

When isoelectric focusing there was obtained a pH-gradient between pH 3.7 and 5.2, which covered 92% of the distance between the electrode solutions.

In column technique as described in Example 1 uniform and low conductivity and UV-absorption curves were obtained over the pH-range 3.7 to 5.2.

EXAMPLE 5

This experiment was carried out in the same manner as that described in Example 1, but with the following amines and amino acids:
0.04 mole of ammonium chloride
0.11 mole of 6-aminocaproic acid
0.08 mole of 4-aminobutyric acid
0.08 mole of β-alanine
0.03 mole of glycine
0.06 mole of glycylglycine
0.07 mole of iminodiacetic acid
0.06 mole if d,l-glutamic acid
0.07 mole of d,l-aspartic acid
0.04 mole of sodium hydroxide.

When isoelectric focusing there was obtained a pH-gradient between pH 2.5 and 5.3, which covered 95% of the distance between the electrode solutions.

In column technique as described in Example 1 uniform and low conductivity and UV-absorption curves were obtained over the pH-range 2.5 to 5.3.

EXAMPLE 6

The synthesis was carried out in the same manner as that described in Example 1, but with the following amines and amino acids:
0.13 mole of ethylenediamine
0.24 mole of β-alanine
0.22 mole of glycine
0.03 mole of glycylglycine.

Subsequent to de-salting, the synthesis was absorbed on 50 g of a cation exchanger having a capacity of 3.0 m equivalents per g (CM Sephadex ® C-25, beads of dextran cross-linked with epichlorohydrin and substituted with carboxymethyl groups; from Pharmacia Fine Chemicals AB, Uppsala, Sweden). The ion exchanger was washed with water, whereafter the ampholyte was freed with 1 molar sodium chloride solution. Subsequent to another desalting, the ampholyte was vaporised in the manner described in Example 1.

When isoelectric focusing there was obtained a pH-gradient between pH 7 and 9 which covered 78% of the distance between the electrode solutions.

In column technique as described in Example 1 uniform and low conductivity and UV-absorption curves were obtained over the pH-range 7 to 9.

EXAMPLE 7

The synthesis was carried out in the same manner as that described in Example 6, but with the following amines and amino acids:
0.075 mole of ammonium chloride
0.068 mole of ethylenediamine
0.050 mole of glycine
0.100 mole of 6-aminocaproic acid
0.075 mole of glycylglycine
0.175 mole of β-alanine
0.075 mole of sodium hydroxide.

In addition, the ampholyte was adsorbed on 150 g of ion exchanger.

When isoelectric focusing there was obtained a pH-gradient between pH 5 and 8 which covered 75% of the distance between the electrode solutions.

In column technique as described in Example 1 uniform and low conductivity and UV-absorption curves were obtained over the pH-range 5 to 8.

EXAMPLE 8

The synthesis was carried out in the same manner as that described in Example 1, but with the following amines and amino acids:
0.10 mole of arginine
0.10 mole of 3,3'-bis-aminopropylamine
0.05 mole of lysine
0.05 mole of N,N-diethylaminoethylamine
0.20 mole of d,l-histidine.

In this case there was used 0.40 mole of epichlorohydrin.

When isoelectrically focusing there was obtained a pH-gradient between pH 8 and 10.5 which covered 80% of the distance between the electrode solutions.

In column technique as described in Example 1 uniform and low conductivity and UV-absorption curves were obtained over the pH-range 8 to 10.5.

EXAMPLE 9

Equal portions of ampholyte solutions prepared in accordance with Examples 5, 7 and 8 above, were mixed together and the mixture tested by isoelectric focusing. There was obtained a pH-gradient between pH 2.5 and 10.5 which covered 95% of the distance between the electrode solutions.

What is claimed is:

1. In a separation process selected from the group consisting of chromatographic processes and electrophoretic processes, including isoelectric focusing and isotachophoresis, in which process an ampholyte is used, the improvement which comprises using as said ampholyte a water-soluble ampholyte containing carboxyl groups and amino groups and comprising a mixture of amphoteric substances, said ampholyte comprising the reaction product obtained by reacting (a) at least two compounds selected from a group containing
    (A) amino acids,
    (B) hydroxylamine,
    (C) an amine of the formula

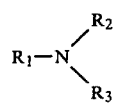

wherein
    —$R_1$ is
       (i) hydrogen, or
       (ii) the group $H_2$—N—$(CH_2)_n$—, wherein n is an integer 2–6, or
       (iii) the group $H_2N$—$(CH_2)_3$—NH—$(CH_2)_3$—$R_2$ and $R_3$ are the same or different and each representing either
       (1) hydrogen,
       (2) methyl,
       (3) ethyl,
       (4) hydroxyethyl, or
       (5) together with the intermediate nitrogen atom form an imidazolyl, morpholinyl- or piperazinyl group, and
    (D) di- and tripeptides said amino acids and said di- and tripeptides containing at least one nitrogen atom having one or two hydrogen atoms bound thereto and not containing aromatic groups other than imidazolyl and having molecular weight of at most 200, at least one of said at least two compounds being one which contains at least one carboxyl group, and/or salts of the aforementioned compounds, and (b) at least one bifunctional alkylating agent having the formula

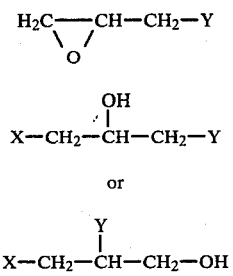

where X and Y are the same or different and each represents a halogen atom, the molar relationship between (b) and (a) being within the range of 1:2–9:10, in an aqueous alkaline medium.

2. A process according to claim 1, wherein X and Y represent chlorine or bromine.

3. A process according to claim 1, wherein the molar relationship between (b) and (a) is 2:3–7:8.

4. A process according to claim 1 or 2, wherein the ampholyte comprises the product obtained by subsequent treatment of said reaction product with a material selected from the group consisting of a haloacetic acid and an alkali metal salt of a haloacetic acid.

5. A water-soluble ampholyte containing carboxyl groups and amino groups and comprising a mixture of amphoteric substances, said ampholyte comprising the reaction product obtained by reacting (a) at least two compounds selected from a group containing (A) amino acids, (B) hydroxylamine, (C) an amine of the formula

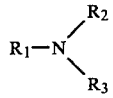

wherein

—$R_1$ is either
  (i) hydrogen,
  (ii) the group $H_2N—(CH_2)_n—$, wherein n is an integer 2–6, or
  (iii) the group $H_2N—(CH_2)_3—NH—(CH_2)_3—R_2$ and $R_3$ are the same or different and each representing either
  (1) hydrogen,
  (2) methyl,
  (3) ethyl,
  (4) hydroxyethyl, or
  (5) together with the intermediate nitrogen atom form an imidazolyl, morpholinyl- or piperazinyl group, and (D) di- and tripeptides, said amino acids and said di- and tripeptides containing at least one nitrogen atom having one or two hydrogen atoms bound thereto and not containing aromatic groups other than imidazolyl and having a molecular weight of at most 200, at least one of said at least two compounds being one which contains at least one carboxyl group, or salts of the aforementioned compounds, with (b) at least one bifunctional alkylating agent having the formula

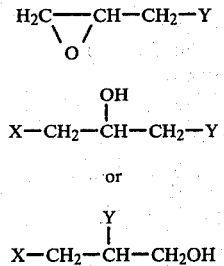

in which X and Y are the same or different and each represents a halogen atom, the molar relationship between (b) and (a) being within the range of 1:2–9:10, in an aqueous alkaline medium.

6. A water-soluble ampholyte according to claim 5, wherein X and Y represent chlorine or bromine.

7. A water-soluble ampholyte according to claim 5, wherein the molar relationship between (b) and (a) is 2:3–7:8.

8. The reaction product of a water-soluble ampholyte according to claim 5 or 6 and a material selected from the group consisting of a haloacetic acid and an alkalimetal salt of a haloacetic acid.

* * * * *